United States Patent [19]

Meuli

[11] Patent Number: 4,556,596
[45] Date of Patent: Dec. 3, 1985

[54] METHOD FOR ADHERING TENSIONED ELASTIC STRIPS TO A FLEXIBLE BASE MATERIAL AND ARTICLE PRODUCED THEREFROM

[75] Inventor: Michael G. Meuli, Menasha, Wis.

[73] Assignee: Kimberly-Clark Corporation, Neenah, Wis.

[21] Appl. No.: 676,920

[22] Filed: Nov. 30, 1984

[51] Int. Cl.⁴ .................. A61F 13/16; B32B 27/08; B32B 31/08

[52] U.S. Cl. .................. 428/152; 2/270; 156/164; 156/229; 428/184; 428/212; 604/385 A

[58] Field of Search .............. 156/164, 229, 244.11, 156/161, 176, 178; 428/212, 152, 184; 604/385 A; 2/270, 76, 78 C

[56] References Cited

U.S. PATENT DOCUMENTS 4,259,220 5/1981 Brunnell et al. .................. 525/98
4,418,123 11/1983 Bunnelle et al. .................. 156/164
4,430,086 2/1984 Repke .................. 60 X/385 A

*Primary Examiner*—Michael Ball
*Attorney, Agent, or Firm*—J. P. O'Shaughnessy; P. Y. Yee

[57] ABSTRACT

A method for applying self-adhering elastic strips to a flexible base material includes adhering a tensioned first strip of the self-adhering elastic material to a flexible base material by sandwiching a less-or untensioned strip of the self-adhering elastic material between the tensioned strip and the base material. Tensioning the first strip in order to impart a sufficiently high degree of elasticization to the base material reduces the inherent strength of adhesion of the strip to the base material. Accordingly, the less-or untensioned intermediate strip insures good adhesion strength of the composite of the two (or more) strips to the base material. The resulting article comprises one having elasticized portions formed by adherence of the tensioned composite strip of self-adhering elastic material thereto.

12 Claims, 6 Drawing Figures

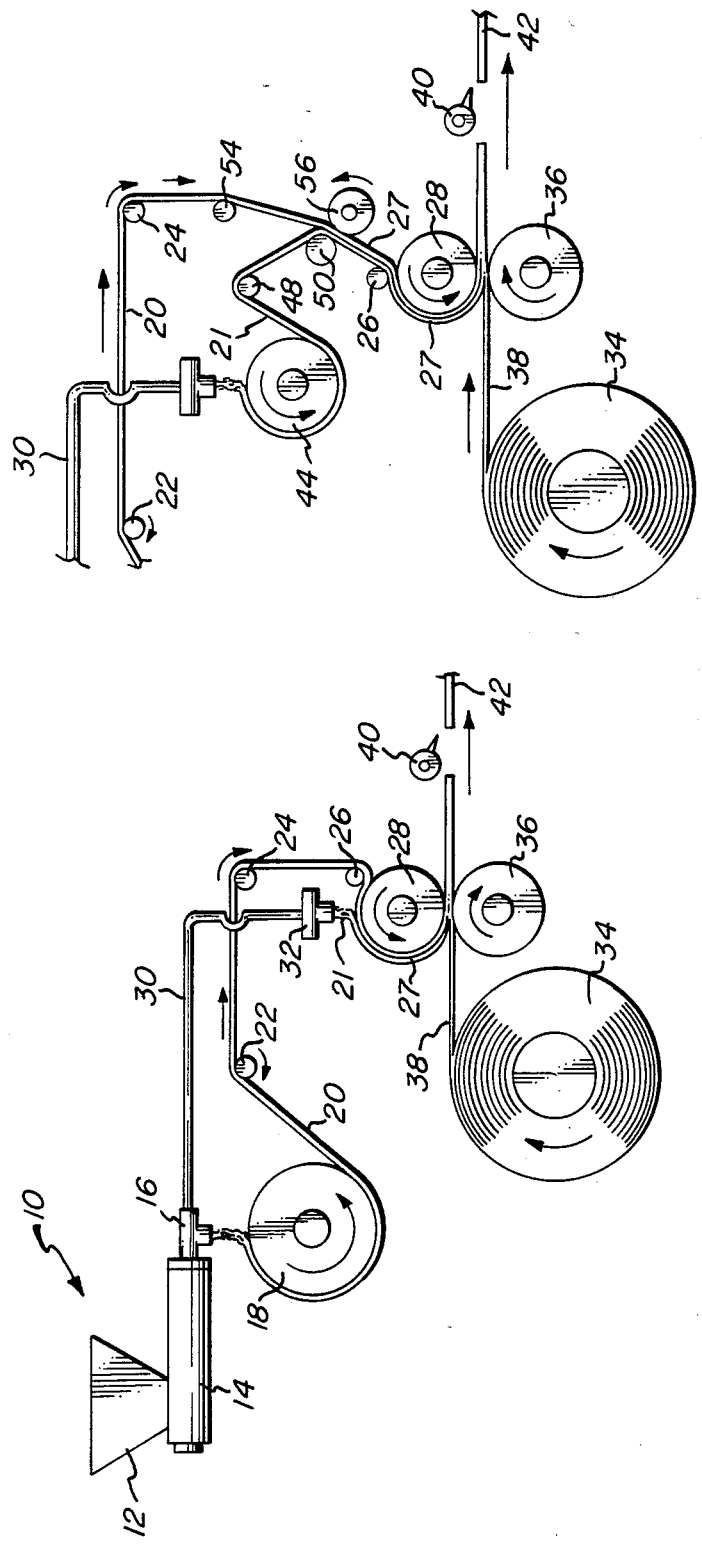

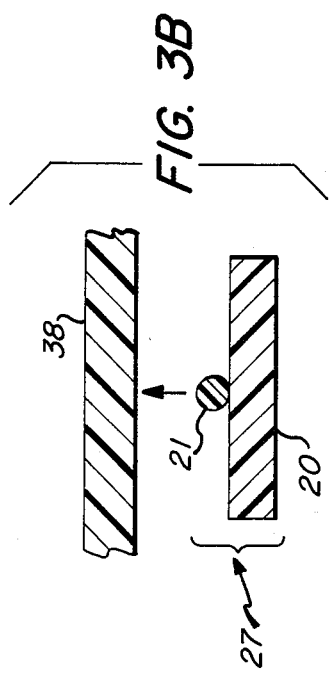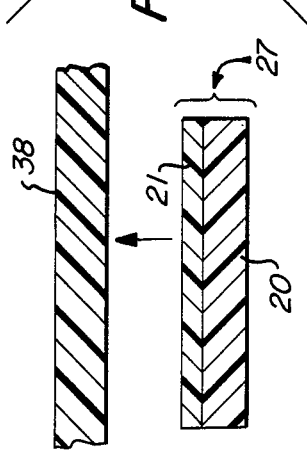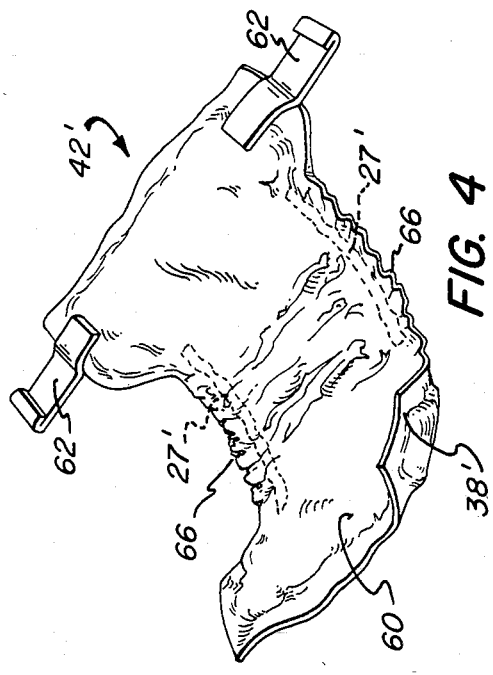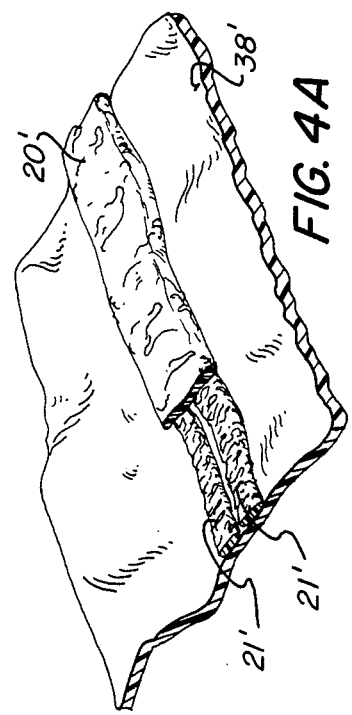

METHOD FOR ADHERING TENSIONED ELASTIC STRIPS TO A FLEXIBLE BASE MATERIAL AND ARTICLE PRODUCED THEREFROM

BACKGROUND OF THE INVENTION

The present invention is concerned with a method of adhering tensioned strips of elastic material to a flexible base material in order to elasticize portions of the base material, and to the elasticized article thereby obtained. The invention finds particular application in elasticizing garments, in particular in elasticizing disposable incontinence control garments, for example, disposable diapers. The manufacture of such articles is usually carried out by joining continuous moving webs of material to form a composite web which is then cut transversely to form the individual articles. It is often desired to elasticize portions of the garments, such as the leg cut-out portions of disposable diapers, in order to provide a snug fit of the diaper about the wearer's legs to aid in controlling or preventing leakage. It is a common expedient in the art to apply bands of elastic material under tension to a moving web or webs of material, utilizing an adhesive, electronic welding, mechanical stitching or any suitable means to secure the tensioned elastic band to the web. Because the elastic band is glued or otherwise secured to the web while held in a tensioned, elongated condition, upon cutting of the web into individual articles the tensioned, elongated elastic bands relax to form elasticized gathers in the flexible material. Generally, any suitable elastic material comprising a suitable rubber, synthetic organic polymeric material or composite material may be utilized as the elastic band.

A particularly useful material for the elastic bands would be one which is both elastic and self-adhering to the flexible base material which is to be elasticized. Such self-adhering elastic material would obviate the need for separate gluing or other securing steps to secure the elastic bands to the flexible base material. Self-adhering elastic materials are known. For example, U.S. Pat. No. 4,259,220 and related U.S. Pat. No. 4,418,123, respectively disclose a viscoelastic, hot melt pressure sensitive adhesive which can be extruded to form a tape which is both pressure sensitive adhesive and elastic, and a method for imparting elastic properties to a flexible substrate by contacting a surface of the substrate with the specified self-adhering elastic material. The disclosure of each of U.S. Pat. No. 4,259,220, issued Mar. 31, 1981 to William L. Bunnelle et al and U.S. Pat. No. 4,418,123, issued Nov. 29, 1983 to William L. Bunnelle et al is incorporated by reference herein.

At least one difficulty exists in utilizing self-adhering elastic materials of the type described in the foregoing U.S. patents to elasticize flexible base materials. This difficulty is that with respect at least to certain base materials such as thin polyolefin sheet material, the greater the degree to which the self-adhering elastic materials are elongated when applied to the base material, the less adherent the self-adhering elastic materials become. In other words, the greater the amount of elongation imposed upon the self-adhering elastic bands applied to the flexible base material, the more the adhesion power of the self-adhering material to the base material is reduced.

SUMMARY OF THE INVENTION

In accordance with the present invention there is provided a method of adhering one or more composite strips of self-adhering elastic material to a flexible base material to elasticize at least selected portions of the base material, the method comprising the following steps: tensioning a first strip of self-adhering elastic material to elongate it whereby the strength of its inherent adhesion to the base material is reduced; joining a less-tensioned second strip of self-adhering elastic material to the elongated first strip to form a tensioned composite strip of self-adhering elastic material, the less-tensioned second strip having a greater strength of adhesion to the base material than the tensioned first strip; and adhering the tensioned composite strip to the base material by joining at least the second strip to the base material.

In one aspect of the invention, the flexible base material is a moving continuous web of material. One specific aspect of the invention includes tensioning the second strip to impose thereon up to 70% of the elongation of the first strip and in any case from 0 to less than 100% elongation, and joining the elongated second strip to the elongated first strip. Another specific aspect of the invention includes tensioning the first strip to impose thereon from about 100% to 400% elongation and optionally tensioning the second strip to impose thereon not more than about 70% elongation.

In certain aspects of the invention the self-adhering elastic material is one comprising (a) a block copolymeric material comprising at least one substantially amorphous, rubbery polymeric midblock and at least one glassy poly(vinylarene) endblock, (b) a midblock associating resin, and (c) an endblock associating resin as described in the aforesaid U.S. Pat. No. 4,418,123.

Other aspects of the invention may comprise one or more of the following: the flexible base material is a polyolefin; the first and second strips of self-adhering elastic material comprise the same material; the method may include the preliminary step of forming strips of self-adhering elastic material in situ from at least one mass of source material and employing the freshly formed strips in the method; and transversely cutting the web of base material into discrete articles containing thereon one or more segments of the composite strip.

In accordance with another aspect of the invention there is provided an article comprising a flexible base material having one or more elasticized portions thereof provided by one or more composite strips of self-adhering elastic material adhered thereto, the composite strips comprising a first strip of self-adhering elastic material adhered to the base material by a second strip of self-adhering elastic material sandwiched between the first strip and the base material, and made by the steps of (a) tensioning a first strip of self-adhering elastic material to elongate it; (b) joining a less-tensioned second strip of self-adhering elastic material to the elongated first strip to form a tensioned composite strip of self-adhering elastic material; and (c) adhering the tensioned composite strip of self-adhering elastic material to the base material by joining at least the second strip to the base material.

The article of the invention may comprise a garment made by the additional steps of adhering the tensioned composite strip to a moving continuous web of the base material and transversely cutting the base material to form the article; the base material may be a polyolefin sheet.

BRIEF DESCRIPTION OF THE DRAWINGS

FIG. 1 is a schematic view in elevation illustrating one embodiment of carrying out the method of the present invention;

FIG. 2 is a partial schematic view in elevation of an alternate embodiment of carrying out the method of the invention;

FIGS. 3A and 3B are schematic end views in section of composite self-adhering elastic strips in accordance with specific embodiments of the invention, shown in juxtaposition to a flexible base material to which the strips are to be applied;

FIG. 4 is a perspective view of an elasticized article made in accordance with the invention and comprising a disposable diaper; and FIG. 4A is a perspective view of a portion of the article of FIG. 4.

DETAILED DESCRIPTION OF THE PREFERRED EMBODIMENTS

FIG. 1 shows in schematic elevation view a method of carrying out one embodiment of the invention wherein an extruder generally indicated at 10 comprises a feed hopper 12 and a screw housing 14 to which is attached an extruder nozzle 16 which is preferably of a type which will produce a relatively wide, flat ribbon of extruded material. Such an extruder nozzle is described, for example, in U.S. Pat. No. 4,389,181 of R. H. Frick, issued June 21, 1983, the disclosure of which is incorporated by reference herein. A suitable material, for example, one as described in the Bunnelle patents incorporated by reference herein, is introduced into hopper 12 and melted to provide a softened plastic extrudable mass of source material from which the strips are formed. A wide flat ribbon of extruded material is deposited from extruder nozzle 16 onto a chill roller 18 which comprises a conventional cooled roller rotating in the direction indicated by the arrow associated therewith and onto which the extruded ribbon is deposited for cooling and setting. Chill roller 18 may be maintained at, say, 0° C. (32° F.) in order to chill a material of the type described in the aforementioned U.S. Pat. Nos. 4,259,220 and 4,418,123. A plurality of extruders or a plurality of extruder nozzles 16 may be arranged to deposit a plurality of extruded ribbons of material onto chill roller 18, as will be appreciated by those skilled in the art. In any event, one or more ribbons 20 of chilled, extruded material are passed to a driven roller 22 which is rotating (in the direction indicated by its associated arrow) at a greater peripheral speed than chill roller 18 whereby the ribbon or ribbons 20 are tensioned and elongated to a desired degree. Ribbon or ribbons 20 are maintained under such tension to hold such elongation by rollers 24 and 26 which also serve to transport the ribbon or ribbons 20 onto joining roller 28 which may, but need not necessarily, be a chill roller.

A heated conduit 30 is connected in fluid flow communication with extruder nozzle 16 and transports a portion of the fluid mass extruded from screw housing 14 to a remote extruder nozzle 32. Remote extruder nozzle 32 may extrude either a wide flat ribbon similar to that extruded from extruder nozzle 16 or may extrude one or more strands of material such as circular or oval cross-section strands. In any event, the material extruded from remote extruder nozzle 32 or a plurality of remote extruder nozzles 32 is deposited upon the extruded ribbon or ribbons 20 in parallel overlying relationship as illustrated in FIGS. 3A and 3B, as described more fully below. Consequently, there is formed on joining roller 28 a plurality of first ribbons 20 of self-adhering elastic material extruded from extruder nozzle 16 and having thereon one or more overlying, parallel second strands 21 of self-adhering elastic material extruded from extruder nozzle 32. As the first strips of self-adhering elastic material are maintained under tension by the rollers 22, 24, 26 and 28 and thereby elongated while the second strands 21 are deposited thereon, there are formed one or more tensioned composite strips 27 of first ribbons 20 and second strips 21 of self-adhering elastic material.

A roll 34 of flexible base material, such as a thin, relatively wide polyolefin material is unwound in the direction indicated by its associated arrow to provide a moving continuous web of base material 38. For example, web 38 may comprise a web of polyolefin material such as polypropylene which is from ½ to 2 mils thick and from 10 to 15 inches (25.4 to 38.1 cm) wide. web 38 is brought into contact with the tensioned composite strips 27 of self-adhering elastic material in the nip formed between joining roller 28 and pressure roller 36 whereby the tensioned composite strips 27 are with and self-adhered to the continuous moving web 38. A cutter 40 may be utilized to cut the web of flexible material 38 into a plurality of discrete articles 42. As the tension of moving continous web 38 is released by the cutting, the adhered tensioned composite strips 27 relax, providing an elasticized gathered portion of the resultant article 42. In the embodiment shown in FIG. 1, the first strips of self-adhering elastic material are tensioned and elongated sufficiently to provide the desired degree of elasticity in the finished articles 42 whereas the second strips of material have not been tensioned and so retain a relatively high degree of self-adherence to the material of flexible web 38. It will be noted that the second strips 21 lie atop the first ribbons 20 upon joining roller 28 so that second strips 21 are sandwiched between the surface of continuous moving web 38 and the first ribbons 20. Since the first ribbons 20 are rendered less adherent to the material of web 38 by virtue of their tensioned, elongated state, untensioned strips 21 of the same material provide enhanced adherence of the composite strips 27 to web 38.

By way of example, a self-adhering elastic material sold by the H. B. Fuller Company of St. Paul, Minn. under the trademark Fullastic 6650 is formed into a one-half inch wide ribbon comprising a first strip in accordance with the invention. A tensioning force of about 200 grams is imposed thereon to provide an elongation of about 270% and thereby a desired degree of elasticization when the ribbon is adhered to a 1.5 mil thick polypropylene web. The second strip may comprise the same material as the first strip and be in the form of a strand of about 0.003 inches (0.076 mm) circular diameter cross-section and have zero tension imposed thereon whereby it retains all of its high inherent adhesion to polypropylene.

Referring now to FIG. 2, there is shown an alternate embodiment in which extruder 10, chill roller 18 and extruder nozzle 16 are identical to those of the FIG. 1 embodiment and thus have been omitted to avoid repetition. Parts in the FIG. 2 embodiment which are identical to those of the FIG. 1 embodiment are identically numbered. Heated conduit 30 is identically connected in fluid flow communication between extruder nozzle 16 (not shown in FIG. 2) and remote extruder nozzle 32 which in this case deposits its extruded strands onto a second chill roller 44 to provide one or more second strips 21 of extruded self-adhering elastic material. A driven roller 48 rotating in the direction indicated by its associated arrow has a higher peripheral speed than does chill roller 44 and therefore second strips 21 are tensioned and elongated to a desired degree which is less than that to which first ribbons 20 are elongated. The degree of tensioning and elongation of second strips 21 are maintained by rollers 50 and 26.

First ribbon 20 obtained from chill roller 18 (not shown in FIG. 2) is tensioned and elongated by driven roller 22 and maintained under such tension and elongation (greater than that of first strips 21) by rollers 24, 54, 50 and 26. The first ribbons 20 and second strips 21 of self-adhering elastic material are joined together in parallel overlying relationship by the nip formed between roller 50 and pressure roller 56 to form a tensioned composite strip 27 which is wound about joining roller 28 which, as in the FIG. 1 embodiment, cooperates with pressure roller 36 to apply composite tensioned strip 27 to continuous moving web 38. Second strips 21 are sandwiched between first ribbon 20 and the material of moving continuous web 38. As in the FIG. 1 embodiment, a cutter 40 may be utilized to cut the moving web of flexible material 38 having the tensioned composite strips 27 joined thereto into discrete articles 42.

Referring now to FIGS. 3A and 3B, alternate embodiments of the composite tensioned strip are illustrated in section end view. FIG. 3A shows an embodiment in which a first strip of self-adhering elastic material 20 comprises a relatively wide flat ribbon and has joined to it a second strip 21 of self-adhering elastic material which is about the same width as first strip 20 (although it could be narrower than strip 20) but considerably thinner. For example, ribbons 20 may be ½ inch (1.47 cm) or ¾ inch (1.91 cm) wide. As indicated by the arrow in FIG. 3A (and FIG. 3B) the resultant tensioned composite strip 27 will be joined to flexible base material 38 with second strip 21 sandwiched between first strip 20 and flexible base material 38.

FIG. 3B illustrates an alternate embodiment in which the tensioned composite strip 27 comprises a ribbon-like first strip 20 identical to that of the embodiment of FIG. 3A having thereon a second strand 21 of self-adhering elastic material comprising a strand of generally circular cross-section which may be, for example, from 25 to 40 thousandths of an inch (0.0635 to 0.102 mm) in diameter. Obviously, two or more parallel strands 21 may be utilized in the FIG. 3B embodiment. It will be noted that in the illustrated embodiments the second strips 21 are disposed in overlying parallel relationship to the first strips 20.

FIG. 4 illustrates an article 42' cut from a moving web of continuous material to which a tensioned composite strip 27 of self-adhering elastic material has been secured. The illustrated article 42' comprises a disposable diaper comprising a thin polypropylene backing sheet 38' cut from a continuous moving web of flexible base material to which has been joined an intermediate absorbent web of material, not visible in FIG. 4, but whose bulk is indicated by the stretch lines on the overlying cover sheet 60. Those skilled in the art will recognize the conventional overall construction of a disposable diaper in which respective webs of backing sheet 38', absorbent material (not shown) and cover sheet 60 are joined in a three-ply layer continuous web which is cut transversely to provide a finished disposable diaper 42'. Conventional adhesive strips 62 are applied for fastening the folded diaper upon the wearer. Composite self-adhering elastic strips 27' of the invention are indicated in dotted lines adjacent the leg cut-outs 66 of diaper 42' and are seen to provide elasticized gathers in the leg cut-out areas.

FIG. 4A shows a schematic view of a portion of composite strip 27' of diaper 42', comprising a ribbon-shaped first strip 20' and a pair of second strips 21' originally of circular cross-section but flattened (by rollers 28 and 36 of FIGS. 1 or 2) and sandwiched between material 38' and first strip 20' to adhere the latter two to each other.

As used herein and in the claims the term "self-adhering elastic material" embraces any otherwise suitable material which is both elastic and self-adherent to the flexible base material to which it is to be adhered and which, upon elongation, becomes less adherent relative to the flexible base material. As used herein and in the claims, the term "flexible base material" means any otherwise suitable material which is flexible enough so that upon adhering of a tensioned elongated elastic material thereto, it will conform to the elastic strip upon relaxation thereof sufficiently to form an elasticized portion of the flexible base material. Reference herein and in the claims to "strips" of self-adhering elastic material is to be understood as including ribbons, bands, strands or other suitable shapes and configurations. Further, all percentage elongations are expressed as a percent of the unelongated or relaxed length of the strip. Thus, 100% elongation means that the untensioned strip has been stretched to twice its relaxed, i.e., untensioned, length. As used herein and in the claims, reference to a "less-tensioned" second strip includes one which is untensioned as well as one which is tensioned but to a percent elongation less than that of the first strip. Similarly, reference to forming the strips "in situ" means that the strips are extruded or otherwise formed at or near the place of application to the web of base material for application thereto without the step of unwinding stored strips from a multiple-ply storage roll. Such "in situ" formation of self-adhering elastic material is convenient because of the difficulty of storing the self-adhering material in multiple-ply rolls from which it can readily be unwound.

In the manufacture of disposable diapers and the like, the flexible base material is conventionally polypropylene, usually of a thickness of from about 1 to 2 mils (e.g., 1 or 1 ½ mils) although other suitable thicknesses and any other suitable material may obviously be employed. Similarly, any suitable self-adhering elastic material may be employed and since the materials described in the aforesaid Bunelle U.S. Pat. Nos. 4,418,123 and 4,259,220 are commercially available and suitable for the purpose, such materials are to that extent preferred.

While the invention has been described in detail with respect to specific preferred embodiments thereof, it will be apparent that upon a reading and understanding of the foregoing other embodiments and modifications may occur to those skilled in the art, which modifications and embodiments are believed to be within the scope of the invention and the appended claims.

What is claimed is:

1. An article comprising a flexible base material having one or more elasticized portions thereof provided by one or more composite strips of self-adhering elastic material adhered thereto, the composite strips comprising a first strip of self-adhering elastic material adhered to the base material by a second strip of self-adhering elastic material sandwiched between the first strip and the base material, and made by the steps of:

(a) tensioning a first strip of self-adhering elastic material to elongate it;

(b) joining a less-tensioned second strip of self-adhering elastic material to the elongated first strip to form a tensioned composite strip of self-adhering elastic material; and (c) adhering the tensioned composite strip of self-adhering elastic material to the base material by joining at least the second strip to the base material.

2. The article of claim 1 comprising a garment and made by the additional steps of adhering the tensioned composite strip to a moving continuous web of the base material and transversely cutting the base material to form the article.

3. The article of claim 2 wherein the base material is a polyolefin sheet.

4. A method of adhering one or more composite strips of self-adhering elastic material to a flexible base material to elasticize at least selected portions of the base material comprises:

tensioning a first strip of self-adhering elastic material to elongate it whereby the strength of its inherent adhesion to the base material is reduced; joining a less-tensioned second strip of self-adhering elastic material to the elongated first strip to form a tensioned composite strip of self-adhering elastic material, the less-tensioned second strip having a greater strength of adhesion to the base material than the tensioned first strip; and adhering the tensioned composite strip to the base material by joining at least the second strip to the base material.

5. The method of claim 4 wherein the flexible base material is a moving continuous web of material.

6. The method of claim 5 including tensioning the second strip to impose thereon up to 70% of the elongation of the first strip and in any case from 0 to less than 100% elongation, and joining the elongated second strip to the elongated first strip.

7. The method of claim 5 including tensioning the first strip to impose thereon from about 100% to 400% elongation and optionally tensioning the second strip to impose thereon not more than about 70% elongation.

8. The method of claim 6 or 7 wherein the self-adhering elastic material is one comprising (a) a block copolymeric material comprising at least one substantially amorphous, rubbery polymeric midblock and at least one glassy poly(vinylarene) endblock, (b) a midblock associating resin, and (c) an endblock associating resin.

9. The method of claim 8 wherein the flexible base material is a polyolefin.

10. The method of claim 4 wherein the first and second strips of self-adhering elastic material comprise the same material.

11. The method of claim 5 including the preliminary step of forming strips of self-adhering elastic material in situ from at least one mass of source material and employing the freshly formed strips in the method.

12. The method of claim 5 including transversely cutting the web into discrete articles containing thereon one or more segments of the composite strip.

* * * * *